| United States Patent [19] | [11] Patent Number: 4,831,152 |
| Itoh et al. | [45] Date of Patent: May 16, 1989 |

[54] 5-HALO-6-NITRO-2-SUBSTITUTED BENZOXAZOLE COMPOUNDS

[75] Inventors: Isamu Itoh; Mitsunori Ono; Hidetoshi Kobayashi; Kazuyoshi Yamakawa, all of Minami-ashigara, Japan

[73] Assignee: Fuji Photo Film Co., Ltd., Kanagawa, Japan

[21] Appl. No.: 744,571

[22] Filed: Jun. 14, 1985

[30] Foreign Application Priority Data

Jun. 15, 1984 [JP] Japan ................. 59-123505

[51] Int. Cl.$^4$ ................. C07D 413/04; C07D 413/06; C07D 413/10
[52] U.S. Cl. ................. 548/224; 546/135; 546/270; 548/217; 548/219; 548/220; 548/222
[58] Field of Search ............... 548/217, 219, 220, 222, 548/224; 546/135, 270

[56] References Cited

U.S. PATENT DOCUMENTS

| 3,880,661 | 4/1975 | Lau et al. | 430/384 |
| 3,912,606 | 10/1975 | Pacifici et al. | 548/217 |
| 4,107,169 | 8/1978 | Schrage | 548/217 |
| 4,254,212 | 3/1981 | Yagihara et al. | 430/553 |
| 4,296,199 | 10/1981 | Yagihara et al. | 430/553 |
| 4,296,200 | 10/1981 | Yagihara et al. | 430/553 |
| 4,299,914 | 11/1981 | Fujimatsu et al. | 430/553 |
| 4,304,844 | 12/1981 | Fujimatsu et al. | 430/553 |
| 4,451,559 | 5/1984 | Sato et al. | 430/553 |
| 4,463,086 | 7/1984 | Sasaki et al. | 430/553 |
| 4,579,813 | 4/1986 | Aoki et al. | 430/553 |
| 4,594,426 | 7/1986 | Fujita et al. | 548/217 |

FOREIGN PATENT DOCUMENTS

| 1149392 | 7/1983 | Canada | 548/217 |
| 10063 | 4/1980 | European Pat. Off. | 548/217 |
| 2314238 | 9/1974 | Fed. Rep. of Germany | 548/217 |
| 3692 | 3/1966 | Japan | 548/217 |

OTHER PUBLICATIONS

Bennett G. Buell, Chem. Abst. 62-5368h.
American Cyanamid Co. Chem. Abst. 61-9616g.
Yokot, Chem. Abst. 95-15924q.
Fuji Photo Film Co. Ltd., Chem. Abst. 95-195120f.
Fujimatsu et al., Chem. Abst. 94-165611d and 165612e.
Yagihara et al., Chem. Abst. 93-85138u.
Elmeligy et al., Chem. Abst. 49618u (1974, vol. 81).
Fuji Photo Film Co. Ltd., Chem. Abst. 103-169823b.
R. Gonner et al., Chem. Abst., vol. 66; 2504a.
Yagihara et al., Chem. Abst. 95-52617n.

Primary Examiner—Donald G. Daus
Assistant Examiner—Cecilia Shen
Attorney, Agent, or Firm—Birch, Stewart, Kolasch & Birch

[57] ABSTRACT

Novel benzoxazole compound having, at the 2 position, a group bonding through a carbon atom having no or one hydrogen atom and introduced with a chlorine or bromine atom at the 5 position. The compounds are key intermediates useful for preparing 2-amino-5-nitrophenol derivatives which are useful as intermediates for synthesis of industrial materials, reducing agents, antioxidants, cyan-image-forming couplers and the like.

18 Claims, No Drawings

5-HALO-6-NITRO-2-SUBSTITUTED BENZOXAZOLE COMPOUNDS

BACKGROUND OF THE INVENTION

1. Field of the Invention

This invention relates to benzoxazole derivatives which are key intermediates useful in producing 2-amino-5-nitrophenol derivatives in which various nucleophilic groups are introduced at the 4 position.

2. Description of the Prior Art

2-Amino-5-nitrophenol derivatives are general-purpose compounds for use as industrial starting materials, and can be converted into synthetic intermediates of higher added value by reduction of the nitro group. The compounds have the o-aminophenol structure which may serve as a reducing agent, and the degree of reducibility can be arbitrarily controlled by introduction of a suitable substituent and conversion of the nitro group into other functional group. In this sense, the derivatives are important as diversity of reducing agents or antioxidants or synthetic intermediates which are convertible into physiologically active compounds by modification of the nitrogen atom.

2-Amino-5-nitrophenol derivatives are also important as synthetic intermediates for cyan-image-forming couplers in the field of photographic chemistry. In recent years, it has been found that 2,5-diacylaminophenol cyan-couplers show good color restoration upon development and the resulting dyes have good fastness to heat and/or humidity (see, for example, Japanese patent application (OPI) Nos. 110530/78, 163537/80 corresponding to U.S. Pat. No. 4,299,914, 29235/81 corresponding to U.S. Pat. No. 4,304,844, 55945/81, 31953/84 corresponding to U.S. Pat. No. 4,463,086 and 31954/84 also corresponding to U.S. Pat. No. 4,463,086, and U.S. Pat. Nos. 4,124,396 and 4,341,864). It has been also found that dyes produced from 2-phenylureideo-5-acylaminophenol cyan-couplers are excellent in color restoration upon development, absorption wavelength, and fastness to heat and/or humidity (see, for example, U.S. Pat. Nos. 4,333,999 and 4,427,767 and Japanese patent application (OPI) Nos. 204543/82, corresponding to U.S. Pat. No. 4,451,559, 204544/82 also corresponding to U.S. Pat. No. 4,451,559 and 204545/82). Accordingly, 2-amino-5-nitrophenol derivatives have attracted attention for use as synthetic intermediates for those couplers.

Photographic couplers may be broadly classified with respect to the hue of dye developed dye. They may also be stoichiometrically classified into two broad classes, i.e. 2-equivalent couplers and 4-equivalent couplers. While 4-equivalent couplers require four moles of silver halide to be developed into one mole of dye, 2-equivalent couplers have a split-off group at the coupling position thereof and can form one mole of dye using two moles of silver halide. For this reason, it is known that 2-equivalent couplers are more beneficial from the standpoint of silver savings. With regard to cyan couplers, for instance, 2-equivalent couplers have such a high color-developing speed that photographic sensitivity is much improved (see, for example, U.S. Pat. Nos. 3,476,563, 3,617,291, 3,880,661, 4,052,212 and 4,147,766, British Pat. Nos. 1,531,927 and 2,006,755, and Japanese patent application (OPI) No. 32071/80 corresponding to U.S. Pat. No. 4,254,212, 1938/81 corresponding to U.S. Pat. No. 4,296,199 and 27147/81 corresponding to U.S. Pat. No. 4,296,200).

As recent color negative films increase in sensitivity, 2-equivalent couplers of high color developing speed, in which slit-off groups are introduced at the coupling position, have been employed in large amounts. Accordingly, of increasing importance are 2-amino-5-nitrophenol derivatives and processes for preparing such derivatives.

As explained above, 2-amino-5-nitrophenol derivatives in which substituents are introduced into the benzene ring are important as industrial starting materials, reducing agents, and intermediates for preparing cyan couplers in photographic chemistry. Preparation of these derivatives is described, for example, in U.S. Pat. No. 3,880,661, and Japanese patent application Nos. 145333/83, 157423/83 corresponding to U.S. Pat. No. 4,579,813, 158470/83, 157424/83, and 199,696/83. One such example may be represented by the following reaction formula (a)

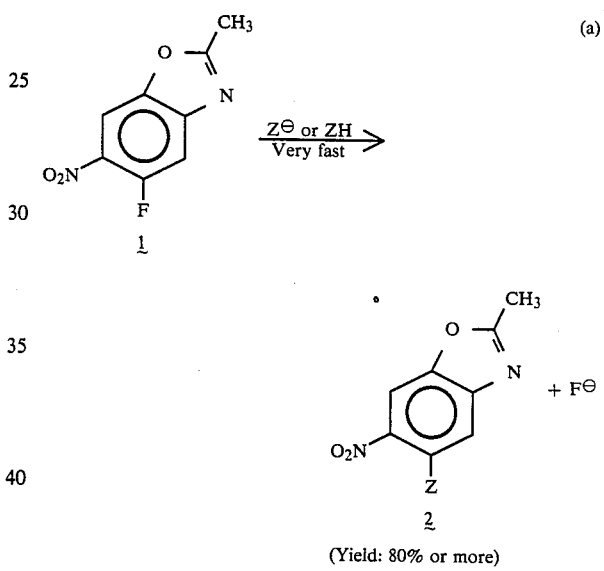

(Yield: 80% or more)

wherein Z represents a nucleophilic group.

The above substitution reaction per se is known as an aromatic nucleophilic substitution reaction. This reaction is described in detail, for example, in Jerry March "Advanced Organic Chemistry" (second edition, (1977) Mcgraw-Hill Kogakusha, Ltd.), chapter 13 entitled "Aromatic Nucleophilic Substitution" pp. 584–595. In the Journal of American Chemical Society, Vol. 79, p. 385 (1957), J. F. Bunnet et al report that the reaction between 2,4-dinitrobenzene derivatives and pyridine proceeds about 3300 times more rapidly when the split-off group is a fluorine atom than when the split-off group is a chlorine or bromine atom.

However, the conventional processes of synthesis, as exemplified as formula (a), have a number of disadvantages.

(1) The fluoro derivative 1 used as the starting material, is obtained by five steps starting from p-fluorophenol and is thus complicated in preparation steps.

(2) The starting p-fluorophenol is not readily available and is expensive.

(3) Because of fluorine ions generated by the reaction, additional plant investment is necessary for safety and water disposal.

(4) The type of material for reactors is limited.

These disadvantages place a serious limitation on mass production. On the other hand, in order to overcome the above disadvantages, it is a matter of course that the reaction formula (a) is effected using, instead of fluoro derivatives (Compound 1), chloro derivatives (Compound 3 below) as described in U.S. Pat. No. 3,880,661.

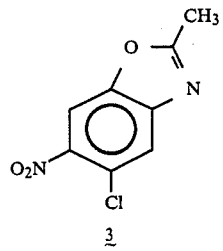

3

This chloro derivative is prepared from 4-chloroaminophenol which are inexpensively available in large amounts. As expected, however, the chloro derivative is much less reactive than the fluoro derivative, thereby giving low yields. Even though the reaction corresponding to formula (a) is carried out using Compound 3 in the presence of a catalyst such as, Cu, CuI, CuI$_2$, CuCl$_2$, CuBr$_2$ and CuO (Ullmann reaction, Fanta, *Synthesis*, 9, 12, 1974), the yield of the desired product (Compound 2) is about 7% maximum with the balance being by-products with unidentified structures.

SUMMARY OF THE INVENTION

In accordance with this invention there are provided novel benzoxazole derivatives in which a specific type of substituent is introduced in the 2 position and which has a chlorine or bromine atom at the 5 position.

Accordingly, it is an object of the invention to provide key intermediates which are prepared from inexpensive, readily available starting materials and which are useful in preparing 2-amino-5-nitrophenol derivatives having optional nucleophilic groups at the 4 position.

It is another object of this invention to provide key compounds from which 2-amino-5-nitrophenol derivatives, introduced with various nucleophilic groups at the 4 position, can be safely prepared using conventional equipment without employing an additional procedure such as treating fluorine ion-containing waste water.

It is a further object of the invention to provide key compounds from which 2-amino-5-nitrophenol derivatives, introduced with proper nucleophilic groups at the 4 position, can be prepared in high yield by reducing the number of steps.

It is a still further object of the invention to provide key compounds which can reduce the production cost of 2-amino-5-nitrophenol derivatives in which various types of nucleophilic groups are introduced at the 4 position.

Other and further objects, features and advantages of the invention will appear more fully from the following description.

DETAILED DESCRIPTION OF THE INVENTION

As a result of extensive studies it has been found that the 2-methyl group of the above-described chloro derivative 3 gives great influences on the substitution reaction and that when the 2-methyl group is replaced by groups other than primary alkyl groups, e.g. secondary alkyl groups, tertiary alkyl groups, aryl groups, heterocyclic residues and the like, substitution reaction with Z$^\ominus$ (or ZH) proceeds smoothly and the desired corresponding substituted products can be obtained in yields as high as 80% or more. Thus, the drawbacks involved in use of fluoro derivatives could be fully overcome.

According to the present invention, there is provided a benzoxazole derivative of general formula [I]

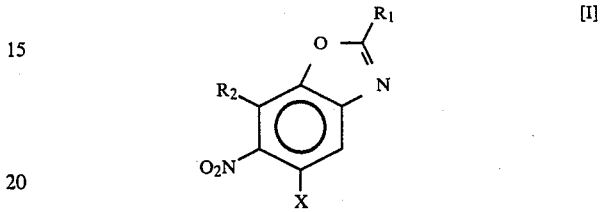

wherein X represents a chlorine atom or a bromine atom, R$_1$ represents a group bonding through a carbon atom having no or one hydrogen atom, and R$_2$ represents a hydrogen atom or a substituent.

R$_1$ in general formula [I] favorably represents an aryl group, a heterocyclic residue bonding through a carbon atom, an alkenyl group, an alkynyl group, a tertiary alkyl group, a secondary alkyl group, an acyl group, a carbamoyl group, an oxycarbonyl group, a carboxyl group, and a ketimine group. Preferable groups as R$_1$ include such moieties that form bis-benzoxazole derivatives. These groups may be further substituted by various substituents.

Preferable substituents which may be introduced into R$_1$ include a halogen atom, a hydroxyl group, an alkoxy group, an aryloxy group, a heterocyclic oxy group, an acyloxy group, an alkyl group, an alkenyl group, an alkynyl group, an aryl group, an amino group, a hydroxylamino group, a carbonamido group, a sulfonamido group, a ureido group, a sulfamido group, an oxycarbonamido group, a carboxyl group, a carbamoyl group, an oxycarbonyl group, a hydroxyaminocarbonyl group, a sulfo group, a sulfamoyl group, a hydroxyaminosulfamoyl group, an alkylsulfonyl group, an arysulfonyl group, a cyano group, a nitro group, and a heterocyclic residue.

Preferable examples of the groups represented by R$_2$ in general formulae [I] include a hydrogen atom, a halogen atom, an alkyl group, an alkenyl group, an aryl group, an alkoxy group, an aryloxy group, an acyloxy group, an amido group, a sulfonamido group, a ureido group, an alkyloxycarbonyl group, a carbamoyl group, a sulfamoyl group, a sulfonyl group, a sulfo group, a cyano group, and a heterocyclic residue. These groups may be further substituted.

The substituents of R$_2$ are preferably the same as those enumerated in group R$_1$.

X in general formula [I] represents a chlorine atom or a bromine atom, of which chlorine atom is preferable in view of its cost and availability.

In the compounds of general formula [I], specific examples of the groups represented by R$_1$ include: aryl group such as phenyl group, 2-chlorophenyl group, 2-methylphenyl group, 2-methoxyphenyl group, 3,4-dichlorophenyl group, 2,5-dichlorophenyl group, pentafluorophenyl group, 4-methoxyphenyl group, 4-t-octylphenyl group, 4-octyloxyphenyl group, 4-dodecylphenyl group, 1-naphthyl group and the like; alkenyl groups such as vinyl group, 2-allyl group, styryl group, 2-furylvinyl group and the like; tertiary alkyl groups such as t-butyl group, 1-methylcyclohexyl group, adamanthyl group, heptafluoropropyl group and the like; secondary alkyl groups such as isopropyl group, 1-ethylpentyl group, cyclohexyl group, 2-norbornyl group and the like; and heterocyclic residues such as 2-furyl group, 3-pyridyl group, 2-quinolyl group and the like.

In more detail, preferable examples of the groups represented by $R_1$ include a group selected from the group consisting of an aryl group, a heterocyclic residue bonding through a carbon atom, an alkenyl group, an alkynyl group, a tertiary alkyl group, a secondary alkyl group, an acyl group, a carbamoyl group, and a ketimine group. Among the groups represented by $R_1$, most preferable examples include a group bonding through a carbon atom having no hydrogen atom.

Specific and most preferable example of the groups represented by $R_1$ is selected from an unsubstituted phenyl group or a phenyl group substituted by at least one group selected from a group consisting of a halogen atom, an alkyl group having 1 to 4 carbon atoms, an alkoxyl group having 1 to 18 carbon atoms, and a tertiary or secondary alkyl group having 3 to 8 carbon atoms.

Preferable examples of the groups represented by $R_2$ in general formula [I] include: hydrogen atom, halogen atoms such as fluorine atom and chlorine atom; alkyl groups such as methyl group, ethyl group, t-butyl group, hexyl group and the like; alkoxy groups such as methoxy group, ethoxy group, 2-methoxyethoxy group, butoxy group and the like; and sulfamoyl groups such as ethylsulfamoyl group, 2-methoxyethylsulfamoyl group and the like.

Specific examples of the compounds of general formula [I] are exemplified only by way of explanation in Table 1.

TABLE 1

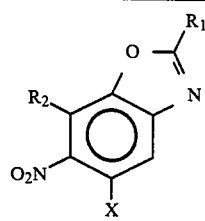

| Compound No. | $R_1$ | $R_2$ | X |
|---|---|---|---|
| (1) | –⟨phenyl⟩ | H | Cl |
| (2) | –⟨naphthyl⟩ | H | Cl |
| (3) | –⟨2-chlorophenyl⟩ | H | Cl |
| (4) | –⟨4-chlorophenyl⟩ | H | Cl |
| (5) | –⟨3,4-dichlorophenyl⟩ | H | Cl |
| (6) | –⟨4-t-butylphenyl⟩–$C_4H_9(t)$ | H | Cl |

TABLE 1-continued

[Structure: benzene ring with O-C(R₁)=N forming oxazole ring, R₂ substituent, O₂N substituent, and X substituent]

| Compound No. | R₁ | R₂ | X |
|---|---|---|---|
| (7) | 2-methoxyphenyl (phenyl with OCH₃) | H | Cl |
| (8) | 4-dodecyloxyphenyl (phenyl with OC₁₂H₂₅) | H | Cl |
| (9) | 2-methylphenyl (phenyl with CH₃) | H | Cl |
| (10) | pentafluorophenyl (C₆F₅) | H | Cl |
| (11) | $-C(CH_3)_3$ (tert-butyl) | H | Cl |
| (12) | $-C(CH_3)_2-C_9H_{19}$ | H | Cl |
| (13) | phenyl | Cl | Cl |
| (14) | 2-furyl | H | Cl |
| (15) | 3-pyridyl | H | Cl |
| (16) | 2-methylquinolin-yl | H | Cl |

TABLE 1-continued

Structure: benzoxazole with $R_1$ at 2-position, $R_2$ and $O_2N$ on benzene ring, $X$ substituent.

| Compound No. | $R_1$ | $R_2$ | X |
|---|---|---|---|
| (17) | cyclohexyl (—CH<) | $CH_3O-$ | Cl |
| (18) | —CH(CH$_3$)$_2$ (isopropyl) | H | Cl |
| (19) | —CH(C$_2$H$_5$)C$_4$H$_9$ | H | Cl |
| (20) | —C(CH$_3$)=CH$_2$ | CH$_3$ | Cl |
| (21) | —CH=CH—phenyl | H | Cl |
| (22) | —CH=CH—(2-furyl) | H | Cl |
| (23) | —C≡CH | H | Cl |
| (24) | —C(=O)—phenyl | $CH_3OCH_2CH_2NHSO_2-$ | Cl |
| (25) | —C$_3$F$_7$ | H | Cl |
| (26) | —C$_8$F$_{16}$H | H | Cl |
| (27) | —C$_3$F$_7$ | Cl | Cl |
| (28) | —CHClCH$_3$ | Cl | Cl |
| (29) | —CH(C$_2$H$_5$)—O—[2,4-di-C$_5$H$_{11}$(t)-phenyl] | H | Cl |
| (30) | phenyl | H | Br |
| (31) | phenyl | Br | Br |
| (32) | —C(CH$_3$)$_3$ | H | Br |
| (33) | —CH(C$_2$H$_5$)C$_4$H$_9$ | H | Br |

TABLE 1-continued
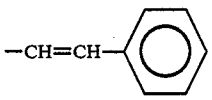
| Compound No. | R₁ | R₂ | X |
|---|---|---|---|
| (34) | 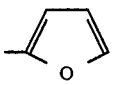 —CH=CH— | H | Br |
| (35) |  | Br | Br |
| (36) | —C₃F₇ | Br | Br |
| (37) | 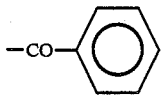 —CO— | H | Br |
| (38) | 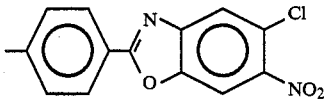 | H | Cl |
| (39) | 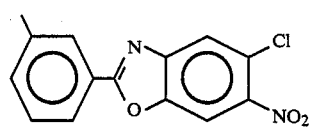 | H | Cl |
| (40) | 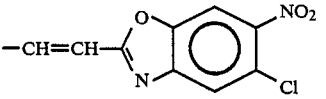 —CH=CH— | H | Cl |
| (41) | 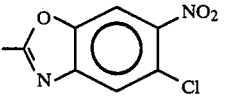 | H | Cl |
| (42) | 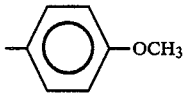 —OCH₃ | H | Cl |
| (43) | 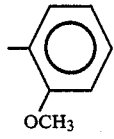 OCH₃ | H | Cl |
| (44) | 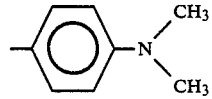 —N(CH₃)₂ | H | Cl |
The compounds of general formula [I] according to the invention are prepared according to the process shown in the following scheme 1.

Scheme 1:

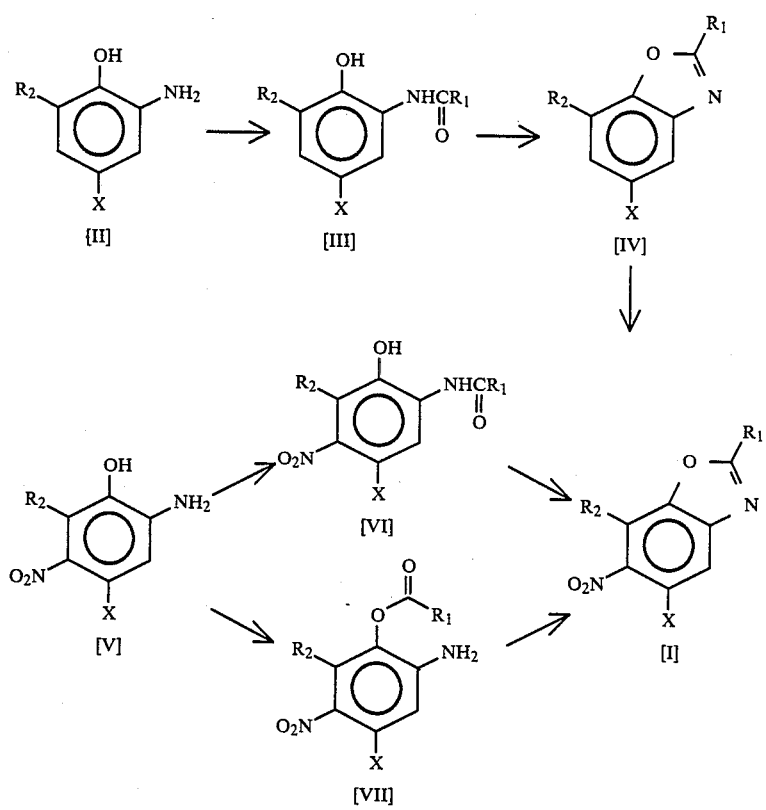

In formulas [II] through [VII] of the scheme 1, $R_1$, $R_2$ and X have, respectively, the same meanings as defined before.

The process shown in the scheme 1 is described in detail.

Compound [I] can be prepared from compound [V] through compound [VII].

Preparation of compound [VII] from aminophenol derivative [V] is achieved by reaction with $R_1COCl$ in the presence of a strong organic base. Preferable examples of the organic base include triethylamine, 1,4-diazabicyclooctane, diazabicycloundecene, diazabicyclononene, 4-(N,N-dimethyl)-pyridine and the like. In general, a hydroxyl group is less reactive with acid chlorides than an amino group. However, if the strong base is present, the oxygen atom alone of the hydroxyl group takes part in the reaction, thereby selectively producing compound [VII]. If the above reaction is carried out in the presence of weak bases such as pyridine, the desired compound [VII] is scarcely obtained but the resulting product is a compund obtained by reaction with the amino group. Thus, the reaction between the compound [V] and $R_1COCl$ varies depending on the type of base, and a desired compound can be obtained by choosing base the appropriately, with an unexpectedly high selectivity being attained.

The reason why the reactions proceed selectively is not known, but it is presumed that the amino group of compound [V] lowers in reactivity due to the nitro group at the para position and X (chlorine or bromine atom) at the meta position with respect to the amino group. However, taking the high selectivity into account, factors other than the lowering of the reactivity are assumed to contribute to the selective formation.

The reaction solvents are not critically limited so far as they are free of active proton. Preferably, solvents having high solubility are employed from the standpoint of productivity. Examples of such solvents include dimethylformamide (DMF), dimethylacetamide (DMAc), N,N-dimethylimidazoline-2-on (DMI), acetonitrile, tetrahydrofuran, chloroform, methylene chloride and the like. The reaction temperature is preferably in the range of from 0° to 80° C. and most preferably from 5° to 50° C. in order to ensure high selectivity.

In order to obtain benzoxazole derivative [I] by ring-closure reaction of compound [VII], the dehydration reaction is effected in the presence of an acid catalyst. The acid catalysts may be all organic and inorganic acids which are ordinarily used in the field of organic synthesis. Preferable examples include organic sulfonic acids such as p-toluenesulfonic acid, methanesulfonic acid and the like, organic carboxylic acids, such as formic acid, trichloroacetic acid, benzoic acid and the like, inorganic acids such as sulfuric acid, phosphoric acid, polyphosphoric acid, sulfur pentaoxide, acid clay and the like, and Lewis acids such as zinc chloride, aluminum chloride, titanium chloride and the like. Suitable solvents for the reaction include those which make azeotrope with water, e.g., aromatic solvents such as xylene, toluene, benzene, anisole and the like, chlorinated solvents such as tetrachloroethane, dichloroethane, methyl chloroform, chloroform and the like, and ether solvents such as diethoxyethane, diglime, dimethoxyethane and the like. In order to increase the solubility, co-solvents may be added including, for example, DMF, DMAc, methyl cellosolve acetate, DMI, diethylene glycol and the like.

Alternatively, compound [I] of the invention may be prepared from the aminophenol compound [II] through compounds [III] and [IV]. This preparation process may be carried out according to the procedure as described, for example, in U.S. Pat. No. 3,880,661.

Still alternatively, the aminophenol compound [V] in which the nitro group has been introduced, may be used as a starting material and converted to an amide compound [IV], followed by ring closure reaction to form compound [I]. However, the conversion of compound [IV] into compound [I] was found to have the following disadvantages: for unknown reasons, this conversion proceeds slowly and thus, it takes a long time (about 8 to 10 hours) before completion of the reaction, so that decomposition reactions take place to form a number of side products and the conversion reaction is unclean; when the reaction temperature is raised to a temperature at which xylene is refluxed (about 140° to 150° C.), the reaction velocity is low; and the reaction solution is intensely colored.

As compared with the above sequence of the reactions, the above-described process in which O-acyl product [VII] is obtained from the aminophenol compound [V] and is then subjected to ring-closure reaction by the use of an acid catalyst, is advantageous in that the dehydration and ring closure reaction is very fast and is completed within a short period of time of about 0.5 to 1.5 hours at relatively low temperatures of about 120° to 130° C. at which toluene is refluxed. Accordingly, coloration of the reaction solution is slight and the yield is high in the reaction. In addition, the amount of an acid catalyst used can be unexpectedly reduced. These effects are considered to be specific ones resulted from the use of O-acyl compound [VII], but the reason why such specific effects are attained is not known.

The compound [I] of the invention can yield, according to the steps shown in the following scheme 2, 2-amino-5-nitrophenol or 2-amino-5-nitrophenol, introduced with nucleophilic groups at the 4 position, being an important intermediate for industrial synthesis.

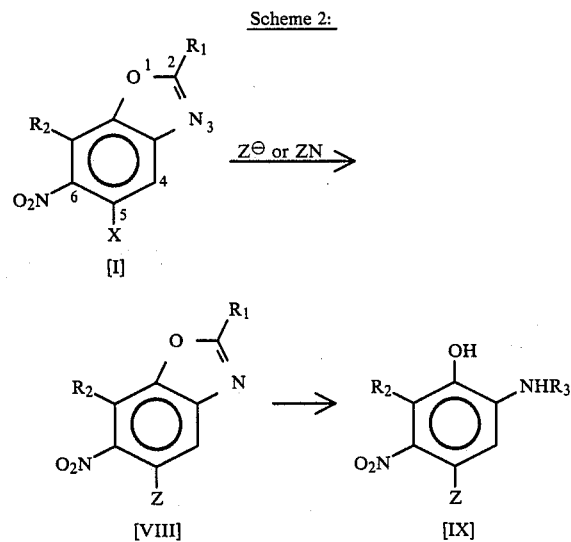

Scheme 2:

In formulae [VIII] and [IX] shown above, $R_1$ and $R_2$ have, respectively, the same meanings as defined with respect to compound [I], Z represents a group obtained by eliminating hydrogen atom from a nucleophilic reagent, and $R_3$ in the formula [IX] represents a hydrogen atom or $-COR_1$ in which $R_1$ has the same meaning as defined before.

Almost all kinds of nucleophilic reagents can be introduced into compound [I] of the invention by nucleophilic substitution reaction. Specific examples of Z include fluorine, a hydroxyl group, an alkoxy group, an aryloxy group, a heterocyclic oxy group, an iminoxy group, an amidoxy group, a sulfonamidoxy group, an acyloxy group, a carbamoyloxy group, a sulfamoyloxy group, a cyanoxy group, an amino group, a carbonamido group, a sulfonamido, a ureido group, a sulfamido group, a hydroxylamino group, an imido group, an azido group, a heterocyclic residue, an alkylthio, an arylthio, a heterocyclic thio group, a cyanothio group, a sulfo group, a sulfothio group, an alkylsulfonyl group, an arylsulfonyl group, a heterocyclic sulfonyl group, an acylthio group, a thiocarbonylthio group, a cyano group, and a methyl group substituted with an electron attractive group. These groups may be further substituted.

Preferable examples of the groups represented by Z include a p-tert-octylphenoxy group and a substituted or unsubstituted phenoxy group, said substituents being selected from the group consisting of a halogen atom, an alkyl group having 1 to 18 carbon atoms and an alkoxy group having 1 to 6 carbon atoms.

In case where Z is introduced by reacting the chlorine or bromine atom of compound [I] of the invention with an oxygen atom, it is desirable to produce an oxygen atom anion and then react it with compound [I]. This is also true in the case of a sulfur atom or the methyl group having electron-attracting group as a substituent. When nitrogen atom is used for Z substitution, it is preferable to use, for reaction with compound [I], ZH where a highly basic nitrogen atom is used, or $Z^\ominus$ where there is used a nitrogen atom whose basicity is low. The substitution reaction may be effected in the presence of metals or metal ions such as Cu, $Cu^+$, $Cu^{2+}$ and the like as is known as the Ullmann reaction. The molar ratio of compound [I] and a nucleophilic agent, ZH is not critical and generally 1:1. One of them, whichever more inexpensive, may be used in excess.

The reaction solvents may be any solvents which are aprotic and are not dissociated or decomposed under alkaline conditions. Preferably, there are used aromatic solvents such as xylene, toluene, anisole, nitrobenzene, benzene and the like, ether solvents such as diglime, dimethoxyethane, dioxane, tetahydrofuran and the like, amide solvents such as DMAc, DMF, DMI, hexamethylphosphoric amide, N-methylpyrrolidone and the like, and halogenated solvents such as dichloroethane, chloroform and the like. The reaction temperature may vary depending on the degree of nucleophilicity of Z, and is generally in the range of from $-40°$ C., to 180° C., preferaby from 0° C. to 140° C.

As described hereinabove, little or no expected reaction takes place using compound 3 in which the chlorine atom as a substituent for the flourine atom is introduced, but only compounds of unidentified structures are produced. In contrast, when compound [I] of the present invention is used, desired substituted compounds can be obtained in high yield as in the case of the fluorine compound 1. This means that the chlorine or bromine atom of compound [I] of the present invention has high reactivity similar to the fluorine atom of compound 1. This is considered to be a quite extraordinary phenomenon. In view of the fact that with chlorine-substituted compounds having, at the 2 position, a primary alkyl group typical example of which is a methyl group, e.g. compound 3, desired compound 2 is scarcely produced but side products of unidentified structures are formed, it is assumed that the oxazole ring per se of compound [I] is much stabilized. However, in a usual compound higher stability results in lower reactivity, which can be disadvantageous in substitution reaction. In this sense, the high reactivity of compound [I] of the present invention is believed to be a rather strange phenomenon which cannot be explained by existing theories.

Compound [I] of the invention is converted to compound [IX], which is a useful intermediate for industrial synthesis, by subjecting the compound to nucleophilic substitution reaction to introduce a nucleophilic group Z at the 5 position, thereby obtaining compound [VIII], and hydrolyzing the thus obtained compound [VIII].

The opening of the benzoxazole ring by hydrolysis is usually under acidic conditions, by which an amino product (general formula [IX], $R_3=H$) is obtained through an amide compound (general formula [VIII], $R_3=COR_1$) (see, for example, the above-indicated U.S. Pat. No. 3,880,661, and Japanese Patent Application (OPI) Nos. 153923/77, 153775/80 and 100771/81).

The ring opening is considered to start from addition of proton to the C=N bond of the benzoxazole ring. The resulting aminophenol product or amidophenol product is kept stable under acidic conditions, so that this process is usually used as a technique of opening benzoxazole or oxazole ring. When compound [VIII] is subjected to the ring-opening reaction according to the methods as described in the above-indicated Japanese Patent Application (OPI) Nos. 153923/77 and 153775/80, or in the presence of other acids such as diluted sulfuric acid, bromine water, iodine water, methanesulfonic acid, p-toluenesulfonic acid, formic acid, acetic acid and the like, compounds of the general formula [IX] in which $R_3=COR_1$ are obtained. However, when the reaction is caused to further proceed until the amido is hydrolyzed, the reaction solution turns into a black tar, so that no aminophenol derivatives of the formula where $R_3=H$ cannot be obtained as crystals. This requires an additional isolation operation using column chromatography. In addition, by-products are contained in large amounts and the yield is at most as small as 10 to 30%.

In such a case, when the reaction is carried out under alkaline conditions, e.g. aqueous NaOH solution, aqueous KOH solution, or CH$_3$ONa, which is exceptional for the ring-opening of benzoxazole, there is rapidly obtained a compound of general formula [IX] where $R_3=H$ through $R_3=COR_1$. Surprisingly, the yield becomes almost quantitative. Thus, with compound [VIII], the ring-opening reaction under alkaline conditions is more convenient, in which the resulting aminophenol product of the formula [IX] where $R_3=H$ is kept more stable. The solvents suitable for hydrolysis are water and aqueous solution of water-miscible solvents. The water-miscible co-solvents are preferably various alcohols (e.g., methanol, ethanol, isopropanol, butanol, methyl cellosolve), and ethers (e.g., diethyl ether, tetrahydrofuran, dioxane, diglime). In order to increase the solubility, co-solvents may be used including, for example, DMSO, SMF, DMAc, DMI, HMPA, acetonitrile and the like. Alternatively, solvents which are immiscible with water (e.g., toluene, benzene, dichloroethane) may be added to form a two phase system. In this case, a phase transfer catalysis, e.g. quaternary ammonium salts, may be used.

The benzoxazole derivatives of the invention have the following advantages.

(1) The derivatives can be prepared using starting materials which are inexpensive and readily available, and can be converted to key intermediates which are useful in preparing 2-amino-5-nitrophenol derivatives introduced with a proper nucleophilic group at the 4 position.

(2) 2-Amino-5-nitrophenol derivatives, which are introduced with a proper nucleophilic group at the 4 position, can be safely prepared from the derivatives of the invention by the use of existing equipments without employing such any additional procedure as treating of fluorine ion-containing waste water.

(3) 2-Amino-5-nitrophenol derivatives, introduced with various nucleophilic groups at the 4 position, can be prepared from the derivatives of the invention by a simple process in high yield.

(4) The 2-amino-5-nitrophenol derivatives can be prepared at reduced production cost.

To further illustrate the invention, and not by way of limitation, the following examples are given.

EXAMPLE 1

Synthesis of Exemplified Compound (1)

(1) Synthesis of (2-amino-4-chloro-5-nitrophenyl)benzoate 377 g (2 moles) of 2-amino-4-chloro-5-nitrophenol and 280 ml (2 moles) of triethylamine were added to 1 liter of N,N-dimethylacetoamide, followed by dropping 281 g (2 moles) of benzoyl chloride at about 50° C. in about 30 minutes. After continuing the agitation for further 30 minutes, 1 liter of methanol and 1 liter of water were added to the reaction solution. The resulting crystals were filtered and washed with 1 liter of methanol, thereby obtaining 547 g (yield 94%) of captioned benzoate compound. m.p. 207°–210° C., IR spectrum $\nu C=0$, 1725 cm$^{-1}$.

(2) Another Way of Synthesis of (2-amino-4-chloro-5-nitrophenyl)benzoate 188 g (1 mole) of 2-amino-4-chloro-5- nitrophenol and 122 g (1 mole) of 4-dimethylaminopyridine were added to 2 liters of acetonitrile, into which 140 g (1 mole) of benzoyl chloride was dropped at room temperature in about 30 minutes. While the temperature of the reaction solution rose up to 50° C., the agitation was continued for 30 minutes. 200 ml of water was added to the reaction solution and the resulting crystals were filtered, followed by washing with 400 ml of 50% methanol, thereby obtaining 245 g of captioned benzoate compound in a yield of 84%. m.p. 208°–210° C.

(3) Synthesis of Exemplified Compound (1)

293 g (1 mole) of benzoate compound obtained in item (1) or (2) and 76 g (0.4 mole) of p-toluenesulfonic acid monohydrate were added to 3 liters of toluene and heated under reflux. The heating under reflux was continued for 1 hour while removing azeotropic water using a water separator. As a result, about 23 ml of water was distilled off. The reaction solution as filtered as heated and then cooled, as it is, at room temperature, followed by further cooling with ice water down to about 10° C., after which the resulting crystals were filtered. The crystals were washed with 2 liters of methanol until the pH of the filtrate was 6–7, thereby obtaining 250 g (yield 91%) of exemplified compound (1). m.p. 199°–201° C.

EXAMPLE 2

Synthesis of Exemplified Compound (6)

A suspension, in 1.5 liters of toluene, of 174 g (0.5 mole) of (2-amino-4-chloro-5-nitrophenol)-4-t-butyl-benzoate prepared in the same manner as in Example 1-(1) and 9.6 g (0.1 mole) of methanesulfonic acid was heated under reflux for about 1 hour, followed by removing azeotropic water by means of a water separator. The reaction solution was cooled down to room temperature and the resulting crystals were filtered, followed by washing the crystals with methanol and water, thereby obtaining 150 g (yield 91%) of light yellowish brown crystals of exemplified compound (6). m.p. 166°–168° C.

EXAMPLE 3

Synthesis of Exemplified Compound (11)

(1) Synthesis of (2-amino-4-chloro-5-nitrophenol)-pivalate

A solution, in 0.5 liters of N,N-dimethylacetamide, of 189 g (1.0 mole) of 2-amino-4-chloro-5-nitrophenol and 153 ml (1.1 moles) of triethylamine was cooled to about 5 to 10° C. by means of iced water, followed by dropping 123 ml (1.0 mole) of pivaloyl chloride in about 1 hour. The reaction solution was agitated for 1 hour, to which 0.5 liters of methanol and 1.0 liter of water were added. The resulting crystals were filtered and added to 2 liters of 30% methanol and agitated well, followed by filtration to obtain 237 g (yield 87%) of light reddish orange crystals of the captioned pivalate. m.p. 135°–137° C.

(2) Synthesis of Exemplified Compound (11)

273 g (1 mole) of pivalate compound obtained in item (1) and 9.5 (0.05 mole) of p-toluenesulfonic acid monohydrate were added to a mixed solvent of 0.5 liters of toluene and 0.2 liters of diglime and heated under reflux for about 2 hours. During the heating, azeotropic water was removed by the use of a water separator and about 24 ml of water was distilled off. When the azeotropy of water terminated, the solvent was completely distilled off under reduced pressure. The resulting oil product was washed with water and remaining p-toluenesulfonic acid was removed, after which 300 ml of n-hexane was added and the resulting crystals were collected by filtration, thereby obtaining 242 g (yield 95%) of exemplified compound (11). m.p. 79°–81° C.

EXAMPLE 4

Synthesis of Exemplified Compound (14)

28.4 g (0.1 mole) of (2-amino-4-chloro-5-nitro)-furoate and 1.9 g (0.01 mole) of p-toluenesulfonic monohydrate were added to a mixed solvent of 200 ml of toluene and 50 ml of diglime and heated under reflux for about 40 minutes, followed by removing azeotropic water by means of a water separator. The reaction solution was cooled down to 10° C. and the resulting crystals were filtered, followed by washing with about 200 ml of cooled methanol, thereby obtaining 22.6 g (yield 85%) of yellow crystals of exemplified compound (14). m.p. over 250° C.

EXAMPLE 5

Synthesis of Exemplified Compound (18)

94.3 g (0.5 mole) of 2-amino-4-chloro-5-nitrophenol and 41 ml (0.53 mole) of pyridine were added to 250 ml of N,N-dimethylacetamide, followed by dropping 53.3 g (0.5 mole) of iso-butyric acid chloride in 30 minutes. The reaction solution was agitated for 1 hour, followed by pouring into 500 ml of water and extracting with 500 ml of ethyl acetate. The extract was dried using Glauber's salt, followed by distilling off ethyl acetate to obtain 103 g of crude crystals (yield about 75%). The product was found to be a mixture of N-acyl and O,N-diacyl compounds. Subsequently, 103 g (about 0.375 mole) of the mixture and 5.7 g (0.03 mole) of p-toluenesulfonic acid monohydrate were added to 400 ml of toluene, followed by heating under reflux. The reaction solution was continually refluxed for about 8 hours until insoluble matters disappeared. After cooling of the reaction solution to room temperature, 300 ml of water and 300 ml of ethyl acetate were added to the solution, followed by separating the aqueous phase and drying the organic phase with Glauber's salt. The solvent was distilled off under reduced pressure and evaporated to dryness, to which methanol was added for crystallization. The crystals were collected by filtration to obtain 48 g (yield 53%) of light yellowish brown crystals of exemplified compound (18). m.p. 80°–81° C.

EXAMPLE 6

Synthesis of Exemplified Compound (19)

94.3 g (0.5 mole) of 2-amino-4-chloro-5-nitrophenol and 74 ml (0.525 mole) of triethylamine were added to 250 ml of N,N-dimethylformamide, followed by dropping, under ice-cold conditions, 81.3 g (0.5 mole) of 2-ethylhexanoyl chloride in about 1 hour. After agitation for 30 minutes, 300 ml of water was added to the reaction solution, followed by extraction twice with each 250 ml of ethyl acetate. The extract was dried with Glauber's salt and subjected to distillation under reduced pressure to obtain 128 g (yield 82%) of an oily O-acyl product. Thereafter, 78.7 g (0.25 mole) of the oily product and 19 g (0.1 mole) of p-toluenesulfonic acid monohydrate were added to 350 ml of toluene, followed by heating under reflux for 1 hour and separating the azeotropic water by a water separator. The reaction solution was cooled, to which 200 ml of ethyl acetate was added, followed by washing with water, drying with Glauber's salt and distilling the solvent off under reduced pressure, thereby obtaining 72 g (yield 97%) of an oily product of exemplified compound (19). Attempts were made to crystallize the oily product by the use of a variety of solvents, but no crystals were obtained.

EXAMPLE 7

Synthesis of Exemplified Compound (21)

75.5 g (0.4 mole) of 2-amino-4-chloro-5-nitrophenol and 58 ml (0.42 mole) of triethylamine were added to 300 ml of N,N-dimethylacetamide, followed by dropping 66 g (0.4 mole) of cinnamic acid chloride at about 5° C. for about 1 hour. After completion of the dropping, the agitation was continued for further 30 minutes, after which the reaction solution was poured into 500 ml of water and the resulting crystals were collected by filtration. The crude crystals were added to 300 ml of acetonitrile and were heated and dispersed at 30° C., followed by filtration to obtain 95.6 g (yield 75%) of cinnamic acid ester. m.p. 184°–186° C.

85.6 g (0.268 mole) of the cinnamic acid ester and 20.4 g (0.107 mole) of p-toluenesulfonic acid monohydrate were added to 300 ml of toluene, and heated under reflux for 1 hour, during which azeotropic water was removed by a water separator. About 200 ml of toluene was distilled off, to which 200 ml of methanol was added, followed by cooling to about 5° C. and filtering the resulting crystals, thereby obtaining 75.7 g of crude crystals. Three liters of acetonitrile was used for recrystallization to obtain 70 g (yield 87%) of light yellowish brown crystals of exemplified compound (21). m.p. 186°–187° C.

EXAMPLE 8

Synthesis of Exemplified Compound (39)

18.8 g (0.1 mole) of 2-amino-4-chloro-5-nitrophenol and 15 ml (0.1 mole) of triethylamine were added to 50 ml of N,N-dimethylacetamide, followed by dropping 10 g (0.05 mole) of isophthalic acid chloride at about 50° C. The agitation was continued for further 1 hour and 50 ml of methanol was added to the reaction solution. The resulting crystals were filtered and dried to obtain 23.2 g (yield 92%) of 1,3-bis(2-amino-4-chloro-5-nitro-phenoxycarbonyl)benzene. m.p. 129°–130° C.

Thereafter, 20.2 g (0.04 mole) of the ester compound was subjected to ring-opening according to the procedure described in Example 1(3), thereby obtaining 15.8 g (yield 84%) of light yellowish brown crystals of exemplified compound (39). m.p. 162°–165° C.

Compounds of the invention were prepared according to the procedure described in Examples 1–8, and the melting point of typical compounds is summarized in Table 2 below.

TABLE 2

| Compound No. | m.p. (°C.) |
| --- | --- |
| (1) | 199–201 |
| (3) | 172–173 |
| (4) | 188–189 |
| (5) | 179–181 |
| (6) | 166–168 |
| (8) | 91–92 |
| (9) | 196–197 |
| (11) | 79–81 |
| (14) | 250 |
| (18) | 80–81 |
| (19)[1] | (oil) |
| (21) | 186–187 |
| (26) | 123–127 |
| (30) | 181–184 |
| (32) | 75–77 |
| (38) | 185–187 |
| (39) | 162–165 |
| (42) | 185–187 |
| (43) | 178–180 |
| (44) | 242–244 |

Note
[1]IR Spectrum of Compound No. (19) 2925, 1608, 1527, 1443, 1345, 1255, 995, 875, 820 (cm$^{-1}$)

The benzoxazole derivatives of general formula [I] of the present invention become very useful key compounds for synthesizing 2-amino-5-nitrophenol derivatives being introduced with various nucleophilic groups at the 4 position. This is particularly described in the following Examples 9–13.

EXAMPLE 9

Synthesis of 2-Amino-5-nitro-4-(4-t-octylphenoxy)phenol 1-(1) Synthesis of captioned compound utilizing exemplified compound (1)

103 g (0.5 mole) of 4-t-octylphenyl and 28 g (0.5 mole) of KOH were added to 1 liter of toluene and heated under reflux for 2 hours, during which azeotropic water was removed by a water separator, thereby obtaining 4-t-octylphenoxy potassium. To the suspension were a solution of 13 g (0.5 mole) of exemplified compound (1) in 0.5 liter of DMF and 3 g of copper powder, followed by heating at 80°–85° C. for 3 hours while agitating. The hot reaction solution was filtered to remove the copper powder, followed by cooling to room temperature. One liter of methanol was added to the reaction solution, followed by cooling to about 10° C. The resulting crystals were collected by filtration to obtain 204 g (yield 92%) of light yellowish brown crystals of 6-nitro-5-(4-t-octylphenoxy)-2-phenylbenzoxazole. m.p. 183°–185° C.

Thereafter, 111 g (0.25 mole) of the benzoxazole and 0.4 liter of an aqueous solution of 40 g (1 mole) of NaOH were added to 1.2 liters of ethanol, followed by heating under reflux for 2 hours in an atmosphere of nitrogen. 0.4 liter of water was added to the reaction solution, which was cooled down to about 15° C., followed by adding about 70 ml of concentrated HCl so that the pH of the reaction solution was adjusted to 6–7. The solution was cooled at 15° C. and the resulting crystals were collected by filtration to obtain 80.6 g (yield 90%) of reddish orange crystals of 2-amino-5-nitro-4-(4-t-octylphenoxy)phenol. m.p. 187°–189° C.

1-(2) Synthesis of captioned compound using exemplified compound (11)

24 g (1 mole) of sodium hydride was added under ice-cold condition to a solution of 206 g (1 mole) of 4-t-octylphenol in 1 liter of toluene, followed by continuing agitation for 1 hour to obtain a sodium salt of 4-t-octylphenol. Subsequently, a solution of 255 g (1 mole) of the exemplified compound (11) in 1 liter of tetrahydrofuran was added to the reaction solution, followed by heating under reflux for 2 hours. After cooling of the reaction solution, about 1 liter of the solvent was distilled off by an evaporator, to which 500 ml of water and 500 ml of ethyl acetate were added for fractionation. The organic phase was dried using Glauber's salt and then the solvent was distilled off to obtain an oily substance. One liter of hexane was added to the oily substance and agitated, followed by collecting the resulting crystals by filtration to obtain 404 g (yield 95%) of light brown crystals of 2-t-butyl-6-nitro-5-(4-t-octylphenoxy)benzoxazole. m.p. 77°–78° C.

To a solution of 213 g (0.5 mole) of the thus obtained benzoxazole compound in 1.5 liters of ethanol were added a solution of 108 g (2 moles) of CH$_3$ONa in 300 ml of methanol, and 700 ml of water, followed by heating under reflux at about 80° C. for 2 hours. One liter of iced water was added to the reaction solution to cool the solution to about 20° C., followed by neutralizing the reaction solution with concentrated HCl to a pH of 6–7. The resulting crystals were filtered, washed with water, and dried to obtain 167 g (yield 93%) of the captioned compound.

1-(3) Synthesis of captioned compound using exemplified compound (14)

A suspension of 0.1 mole of 4-t-octylphenoxy potassium, prepared in the same manner as in 1-(1), in 150 ml of toluene was provided, to which a solution of 26.6 g (0.1 mole) of exemplified compound (14) in 50 ml of N,N-dimethylacetamide, and 0.1 g of cupric chloride, followed by heating at 80° C. for 2 hours under agitation. About 120 ml of the toluene was distilled off under reduced pressure, and 200 ml of methanol was added to the residue, which was cooled down to about 10° C.

The resulting crystals were filtered to obtain 35.4 g (yield 82%) of light yellow crystals of 2-furyl-6-nitro-5-(4-t-octylphenoxy)benzoxazole. m.p. 146°-148° C.

Subsequently, 21.6 g (0.05 mole) of the thus obtained benzoxazole compound was hydrolyzed with 4 equivalents of NaOH in the same manner as described in 1-(1), followed by neutralization with concentrated HCl and crystallization, thereby obtaining 16.3 g (yield 91%) of captioned compound.

1-(4) Synthesis of captioned compound using exemplified compound (19)

A suspension of 0.1 mole of 4-t-octylphenoxy potassium, obtained in the same manner as in 1-(1), in 150 ml of toluene was provided, to which a solution of 29.7 g (0.1 mole) of an oil of exemplified compound (19) in 20 ml of N,N-dimethylformamide was added, followed by heating at about 80° C. for 2 hours with agitation. The reaction solution was cooled down to room temperature, to which 150 ml of ethyl acetate and 100 ml of water were added. The organic phase was separated, dried with Glauber's salt, and subjected to distillation under reduced pressure, thereby obtaining 48 g of a crude oily benzoxazole product. Polar components were removed by silica gel chromatography, thereby obtaining 38.3 g (yield 82%) of pure 2-(1-ethylphentyl)-6-nitro-5-(4-t-octylphenoxy)benzoxazole, which gave one spot on TLC. 37 g (0.08 mole) of the oil product was added to 150 ml of methanol, to which a solution of 17 g (0.32 mole) of $CH_3ONa$ in 45 ml of methanol, and 70 ml of water were added, followed by heating under reflux for 2 hours. 100 ml of water was added to the reaction solution and neutralized with acetic acid to a pH of about 7, followed by cooling down to about 10° C. The resulting crystals were filtered and dried to obtain 26.7 g (yield 93%) of the captioned compound.

1-(5) Synthesis of captioned compound using exemplified compound (21)

A suspension of 0.1 mole of 4-t-octylphenoxy potassium, prepared in the same manner as in 1-(1), in 150 ml of toluene was provided, to which a solution of 30 g (0.1 mole) of exemplified compound (21) in 30 ml of diethylene glycol dimethyl ether was added, followed by heating at about 90°-100° C. for 1.5 hours under agitation. Thereafter, 200 ml of methanol was added to the reaction solution, which was cooled down to about 15° C. The resulting crystals were filtered and dried to obtain 41.4 g of light yellowish brown crystals of 6-nitro-5-(4-t-octylphenoxy)-2-styrylbenzoxazole. m.p. 159°-162° C.

23.5 g (0.05 mole) of the above crystals were hydrolyzed using 4 equivalents of NaOH in the same manner as in 1-(1), thereby obtain 16.3 g (yield 91%) of the captioned compound.

1-(6) Synthesis of captioned compound using exemplified compound (32)

A suspension of 0.1 mole of t-octylphenoxy potassium, prepared in the same manner as in 1-(1), in 150 ml of toluene was provided, to which a solution of 30 g (0.1 mole) of exemplified compound (32) in 50 ml of diethylene glycol dimethyl ether was added, followed by heating at 90° C. for 2 hours under agitation and distilling off about 130 ml of toluene under reduced pressure. To the reaction solution were added 200 ml of ethanol and 150 ml of an aqueous solution of 16 g (0.4 mole) of NaOH, followed by heating at about 80° C. under reflux. 100 ml of iced water was added to the reaction solution, followed by adjusting the pH to 6-7 by means of concentrated hydrochloride acid. The resulting crystals were filtered to obtain 29.5 g (total yield 82%) of the captioned compound.

1-(7) Through process of synthesizing the captioned compound through exemplified compound (11)

273 g (1 mole) of (2-amino-4-chloro-5-nitrophenyl)-pivalate and 9.5 g (0.05 mole) of p-toluenesulfonic acid monohydrate were added to 800 ml of toluene and heated under reflux for 1 hour, during which about 22 ml of water was distilled off to obtain exemplified compound (11). Subsequently, 500 ml of toluene was distilled off under reduced pressure, 80 ml of diethylene glycol dimethyl ether was added to the reaction solution. This reaction solution was added, in an atmosphere of nitrogen, to a suspension of 261 g (1 mole) of a potassium salt of 4-t-octylphenol in 400 ml of toluene, followed by diluting with 80 ml of diethylene glycol dimethyl ether. The reaction solution was heated at 80° C. for 1.5 hours and then 500 ml of toluene was removed by distillation under reduced pressure. To the reaction solution were added 800 ml of ethanol and 250 ml of a solution of 160 g (4 moles) of NaOH, followed by heating under reflux for 2 hours. The reaction solution was cooled down to room temperature, to which 500 ml of water and 100 ml of ethanol were added, followed by adjusting the pH of the reaction solution to 5-6 by means of concentrated hydrochloric acid. The resulting crystals were filtered and washed with water to obtain 243 g of the captioned compound (total yield 68%) as reddish orange crystals.

As will be understood from the foregoing, 2-amino-5-nitro-4-(4-t-octylphenoxy)phenol can be prepared in high yield by the use of the compounds of the present invention. Other typical compounds are shown in Table 3 below with respect to the melting point of substituted products, and yields in the substitution reaction and hydrolysis.

TABLE 3

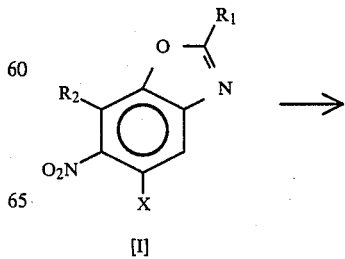

[I]

TABLE 3-continued

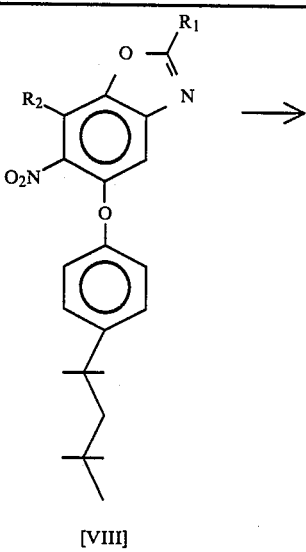

[VIII]

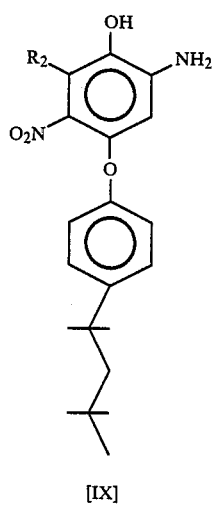

[IX]

| Compound No. | [I] → [VIII] yield (%) | [VIII] m.p. (°C.) | [VIII] → [IX] yield (%) |
|---|---|---|---|
| (4) | 91 | 220–224 | 93 |
| (5) | 90 | 140–142 | 91 |
| (6) | 93 | 175–177 | 89 |
| (8) | 85 | 81–83 | 87 |
| (9) | 94 | 111–113 | 93 |
| (13) | 88 | 125–128 | 92 |
| (18) | 82 | 80–81 | 95 |
| (30) | 91 | 185–187 | 90 |
| (39) | 89 | 163–166 | 91 |

For comparison, compounds of general formula [I] which are outside the scope of the invention and which include compound 3 having a methyl group, in which the number of substitution of hydrogen atoms of 3, as a substituent corresponding to R₁, and compound 4 having an undecyl group in which the number of substitution of hydrogen atom is 2, are described.

COMPARATIVE EXAMPLE 1-(1)

According to the procedure described in Example 9-(1), 21.2 g (0.1 mole) of known 5-chloro-2-methyl-6-nitrobenzoxazole in 100 ml of DMF and 0.6 g of copper powder were added to a suspension of 0.1 mole of 4-t-octylphenoxy potassium in 150 ml of toluene, and heated to about 80° C. The reaction solution immediately turned into bluish purple color, thereby precipitating an insoluble matter. The solution was heated for 2 hours as it is, followed by removing the insoluble matter by filtration. About 18 g of the thus obtained insoluble matter was found to be a side product of an unidentified structure. 200 ml of ethyl acetate and 200 ml of water were added to the filtrate, and the organic phase was separated, dried with Glauber's salt, and distilled under reduced pressure to obtain about 6 g of a blackish brown solid matter. The thus obtained solid matter was isolated and purified by silica gel chromatography to obtain 2.3 g (yield 7%) of a yellowish brown substituted product.

COMPARATIVE EXAMPLE 1-(2)

The procedure of Comparative Example 1-(1) was repeated except that no copper powder (0.6 g) was used. As a result, it was found that no substitution reaction proceeded and a mixture of side products of unidentified structures was obtained.

COMPARATIVE EXAMPLE 1-(3)

The procedure of Comparative Example 1-(1) was repeated using 35.3 g (0.1 mole, m.p. 34°–36° C.) of 5-chloro-6-nitro-2-undecylbenzoxazole (Compound 4) instead of 5-chloro-2-methyl-6-nitrobenzoxazole. As a result, there was obtained a sparingly soluble mixture of products having unidentified structures, but no desired product was obtained.

As described in the above comparative examples, compounds other than those compounds of the present invention involve reactions other than the substitution reaction, so that desired substituted products are scarcely obtained. In contrast, the compounds of the invention yield substituted products in yields over 90%. From the above fact, the specificity of the compounds of the invention will be clear.

EXAMPLE 10

Synthesis of 2-amino-4-(4-methoxyphenoxy)-5-nitrophenol 2-(1) Synthesis of the captioned compound using exemplified compound (5)

124 g (1 mole) of 4-hydroxyanisole and 38.8 g (1 mole) of potassium hydroxide were added to 1.4 liters of toluene and heated under reflux for 3 hours, during which azeotropic water was separated using a water separator, thereby obtaining potassium salt of 4-hydroxyanisole. To the reaction solution was added 700 ml of a solution of 342 g (1 mole) of exemplified compound (5) in N,N-dimethylformamide, followed by heating at about 85° C. for 3.5 hours. Thereafter, 1.5 liters of methanol was added to the reaction solution, followed by cooling to about 10° C. The resulting crystals were collected by filtration to obtain 374 g (yield 87%) of yellowish brown crystals of 2-(2,4-dichlorophenyl)-5-(4-methoxyphenoxy)-6-nitrobenzoxazole. m.p. 144°–146° C.

215 g (0.5 mole) of the thus obtained benzoxazole compound was hydrolyzed with 4 equivalents of NaOH in the same manner as in Example 9-(1), thereby obtaining 127 g (yield 92%) of the captioned compound. m.p. 198°–199° C.

2-(2) Synthesis of captioned compound using exemplified compound (30)

A suspension of 0.1 mole of 4-methoxyphenoxy potassium in 140 ml of toluene was prepared in the same manner as in item 2-(1). To the suspension was added 70 ml of a N,N-dimethylformamide solution of 32 g (0.1 mole) of exemplified compound (30), which was heated at about 90° C. for 2 hours. Thereafter, 150 ml of methanol was added to the reaction solution and cooled down to about 15° C. The resulting crystals were filtered and dried to obtain 32.2 g (yield 89%) of 5-(4-methoxyphenoxy)-6-nitro-2-phenylbenzoxazole as light yellowish brown crystals. m.p. 142°–146° C.

18 g (0.05 mole) of the thus obtained benzoxazole compound was hydrolyzed with 4 equivalents of NaOH in the same manner as in Example 9-(1), thereby containing 13.1 g (yield 95%) of the captioned compound.

EXAMPLE 11

Synthesis of 2-amino-4-(4-methanesulfonylphenoxy)-5-nitrophenol 34.2 g (0.24 mole) of 4-methylthiophenol and 16.1 g (0.24 mole) of potassium hydroxide were added to 350 ml of toluene, followed by heating under reflux and removing produced water by a water separator, thereby obtaining potassium salt of 4-methylthiophenol. To the potassium salt were added 67.1 g (0.244 mole) of exemplified compound (1) and 0.1 g of copper powder, followed by heating under reflux for 2 hours. About 300 ml of toluene was distilled off under reduced pressure, and the resulting concentrate was filtered as heated and poured into 400 ml of methanol. The resulting crystals were filtered, washed with methanol and dried to obtain 80.2 g (yield 88%) of 5-(4-methylthiophenoxy)-6-nitro-2-phenylbenzoxazole. m.p. 163°–165° C.

Subsequently, 17 g (0.045 mole) of the thus obtained benzoxazole compound was dispersed in 200 ml of methylene chloride, to which 23.3 g (0.095 mole) of meta-chloroperbenzoic acid was added portion by portion under ice-cold conditions. The crystals were once dissolved but fresh crystals appeared. After agitation of 1 hour, the crystals were filtered, washed with an aqueous sodium sulfite solution, an aqueous sodium hydrogencarbonate solution, water and methanol, and dried to obtain 18 g (yield 97%) of 5-(4-methanesulfonylphenoxy)-6-nitro-2-phenylbenzoxazole. m.p. 235°–242° C.

16.5 g (0.04 mole) of the benzoxazole compound was hydrolyzed with 4 equivalents of NaOH in the same manner as described in Example 1-(1), thereby obtaining 12.2 g (yield 94%) of the captioned compound. m.p. 123°–125° C.

In the same manner as in Examples 9–11, various types of phenoxy-substituted products are prepared from the compounds of the invention, and are converted into corresponding aminophenol derivatives by subsequent hydrolysis.

Typical phenoxy-substituted products produced from exemplified compound (1) are shown in Table 4 with regard to the melting point.

TABLE 4

| Z | m.p. (°C.) |
|---|---|
| —O—C6H5 | 148–150 |
| —O—(2,4-Cl2-C6H3) | 158–160 |
| —O—(2-OCH3-C6H4) | 153–155 |
| —O—(3-OCH3-C6H4) | 151–154 |
| —O—(4-OH-C6H4) | 213–215 |
| —O—(4-OC4H9-C6H4) | 112–114 |
| —O—(4-OCH2CH2OCH3-C6H4) | 116–118 |
| —O—(4-C4H9(t)-C6H4) | 180–183 |
| —O—(4-C5H11(t)-C6H4) | 155–157 |
| —O—(2,4-(C5H11(t))2-C6H3) | 150–152 |

TABLE 4-continued

| Z | m.p. (°C.) |
|---|---|
| ![structure -O-phenyl-C15H31] | 65-66 |

EXAMPLE 12

Synthesis of 2-amino-4-(4-dodecylphenylthio)-5-nitrophenol

In the same manner as in Example 9-(2), a suspension of 30 g (0.1 mole) of sodium salt of 4-dodecylthiophenol in 200 ml of toluene was prepared, into which a solution of 29.6 g (0.1 mole) of exemplified compound (19) in 50 ml of DMF was dropped. While the reaction temperature was kept at 50°-60° C., agitation was continued for 1 hour. Thereafter, 200 ml of water was added to the reaction solution, which was extracted twice with 200 ml of ethyl acetate. The extract was dried with Glauber's salt, from which the solvent was distilled off by means of an evaporator, thereby obtaining 51.8 g (yield 96%) of an oil of 5-dodecylthio-2-(1-ethylpentyl)-6-nitrobenzoxazole. This oil was hydrolyzed with 4 equivalents of NaOH in the same manner as in Example 9-(1), thereby obtaining 38.4 g (yield 93%) of the captioned compound. m.p. 108°-110° C.

Mercapto compounds were substituted in the same manner as in Example 11, and converted into corresponding aminophenol compounds by subsequent hydrolysis. The melting point of typical compounds are shown in Table 5 below.

TABLE 5

| Z | (nitrobenzoxazole structure) | (aminophenol structure) |
|---|---|---|
| —S—C$_{16}$H$_{33}$ | 73-75° C. | 116-117° C. |
| —S—CHCOOC$_2$H$_5$ $\quad$ C$_{12}$H$_{25}$ | 52-55° C. | 115-117° C.* |
| —S—(phenyl with OC$_4$H$_9$ and C$_8$H$_{17}$(t)) | 138-140° C. | 138-140° C. |

*After hydrolysis, esterification was effected to give an ethyl ester.

EXAMPLE 13

Synthesis of 2-amino-4-morpholino-5-nitrophenol 54.9 g (0.2 mole) of exemplified compound (1) was added to 200 ml of morpholine, followed by heating on a steam bath for 8 hours. The reaction solution was cooled, to which 500 ml of water was added. The resulting crystals were filtered and washed with 350 ml of 20% methanol solution, thereby obtaining 69.5 g (yield 96%) of 5-morpholino-6-nitro-2-phenylbenzoxazole as light brown crystals. m.p. 134°-135° C.

50 g (0.153 mole) of the thus obtained benzoxazole compound and 40 g (0.612 mole) of KOH were added to 1 liters of 75% ethanol, followed by heating under reflux for 2 hours. Thereafter, 200 ml of water was added to the reaction solution, followed by cooling to about 10° C. and adjusting the pH to 5-6 by means of concentrated HCl. The resulting crystals were filtered and dried to obtain 32 g (yield 86%) of red crystals of the captioned compound. m.p. 191°-192° C.

Having described a specific embodiment of our invention, it is believed that any modification or variation of our invention is within the scope of the present invention in light of the above teachings.

What is claimed is:

1. A benzoxazole compound of the following formula:

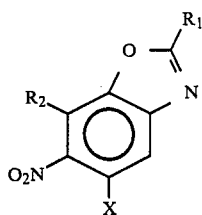

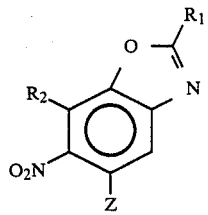

wherein X represents a chlorine atom or a bromine atom, R₁ represents a group selected from the group consisting of a lower alkynyl group, a tertiary alkyl group having 4–10 carbon atoms, a 1-methylcyclohexyl group, an adamanthyl group, a heptafluoropropyl group, a secondary alkyl group having 3–7 carbon atoms, a cyclohexyl group, a 2-norbornyl group, an acyl group of a carboxylic acid, a carbamoyl group, a ketimine group, a fluorinated alkyl group having 1–8 carbon atoms, a styryl group, a 2-furylvinyl group, an alkenyl group selected from the group consisting of a vinyl group and a 2-allyl group, a heterocyclic residue selected from the group consisting of a 2-furyl group, a 3-pyridyl group, and a 2-quinolyl group, an unsubstituted phenyl group, a phenyl group substituted with a tertiary alkyl group having 4–8 carbon atoms, and a phenyl group directly substituted by one or more groups selected from the group consisting of halogen atoms, an alkyl group having 1–12 carbon atoms, an alkoxyl group having 1–18 carbon atoms, a secondary alkyl group having 3–8 carbon atoms, a N(CH₃)₂ group, and a ketimine group, wherein the number of hydrogen atoms bonded to a carbon atom through which R₁ bonds is either one or zero and R₂ represents a substituent selected from the group consisting of a hydrogen atom, a halogen atom, a lower alkyl group, an alkenyl group selected from the group consisting of a vinyl group and a 2-allyl group, an alkoxy group having 1–18 carbon atoms, a 2-methoxyethoxy group, an ethylsulfamoyl group, a 2-methoxyethylsulfamoyl group, an acyloxy group of a carboxylic acid, an amido group, a sulfonamido group, an ureido group, an alkyloxycarbonyl group, a carbamoyl group, a sulfamoyl group, a sulfonyl group, a sulfo group, a cyano group, and an aryloxy group with the proviso that said aryloxy group is not heteroaromatic.

2. The benzoxazole compound as in claim 1, wherein said R₁ group bonds through a carbon atom having no hydrogen atoms.

3. The benzoxazole compound as in claim 1, wherein X represents a chlorine atom.

4. The benzoxazole compound as in claim 1, wherein X represents a bromine atom.

5. The benzoxazole compound as in claim 1, wherein R₂ represents a hydrogen.

6. 5-Chloro-6-nitro-2-phenylbenzoxazole according to claim 1.

7. 2-tert-Butyl-5-chloro-6-nitrobenzoxazole according to claim 1.

8. 5-Chloro-2-furyl-6-nitrobenzoxazole according to claim 1.

9. 5-Chloro-6-nitro-2-styrylbenzoxazole according to claim 1.

10. A benzoxazole compound of the following formula:

wherein Z represents a nucleophilic group, R₁ represents a group selected from the group consisting of a lower alkynyl group, a tertiary alkyl group having 4–10 carbon atoms, a 1-methylcyclohexyl group, an adamanthyl group, a heptafluoropropyl group, a secondary alkyl group having 3–7 carbon atoms, a cyclohexyl group, a 2-norbornyl group, an acyl group of a carboxylic acid, a carbamoyl group, a ketimine group, a fluorinated alkyl group having 1–8 carbon atoms, a styryl group, a 2-furylvinyl group, an alkenyl group selected from the group consisting of a vinyl group and a 2-allyl group, a heterocyclic residue selected from the group consisting of a 2-furyl group, a 3-pyridyl group, and a 2-quinolyl group, an unsubstituted phenyl group, a phenyl group substituted with a tertiary alkyl group having 4–8 carbon atoms, and a phenyl group directly substituted by one or more groups selected from the group consisting of halogen atoms, an alkyl group having 1–12 carbon atoms, an alkoxy group having 1–18 carbon atoms, a secondary group having 3–8 carbon atoms, a N(CH₃)₂ group, and a ketimine group, wherein the number of hydrogen atoms bonded to a carbon atom through which R₁ bonds is either one or zero and R₂ represents a substituent selected from the group consisting of a hydrogen atom, a halogen atom, a lower alkyl group, an alkenyl group selected from the group consisting of a vinyl group and a 2-allyl group, an alkoxy group having 1–18 carbon atoms, a 2-methoxy-ethoxy group, an ethylsulfamoyl group, a 2-methoxyethylsulfamoyl group, an acyloxy group of a carboxylic acid, an amido group, a sulfonamido group, an ureido group, an alkyloxycarbonyl group, a carbamoyl group, a sulfamoyl group, a sulfonyl group, a sulfo group, a cyano group, and an aryloxy group with the proviso that said aryloxy group is not heteroaromatic.

11. The benzoxazole compound as in claim 10, wherein Z represents a p-tert-octylphenoxy group.

12. The benzoxazole compound as in claim 10, wherein Z represents a substituted or unsubstituted phenoxy group, said substituents being selected from the group consisting of a halogen atom, an alkyl group having 1 to 18 carbon atoms and an alkoxy group having 1 to 6 carbon atoms.

13. The benzoxazole compound as in claim 1, wherein R₂ is a hydrogen atom, a halogen atom selected from the group consisting of a fluorine atom and a chlorine atom; an alkyl group selected from the group consisting of a methyl group, an ethyl group, a t-butyl group, and a hexyl group; an alkoxy group selected from the group consisting of a methoxy group, an ethoxy group, and a butoxy group.

14. The benzoxazole compound as in claim 1, wherein R₂ is a member selected from the group consisting of a hydrogen atom, halogen atoms, alkyl groups, alkoxy groups, and sulfamoyl groups.

15. The benzoxazole compound as in claim 1, wherein R₁ is a substituted phenyl group selected from the group consisting of a phenyl group, a 2-chlorophenyl group, a 2-methylphenyl group, a 2-methoxyphenyl group, a 3,4-dichlorophenyl group, a 2,5-dichlorophenyl group, a pentafluorophenyl group, a 4-methoxyphenyl group, a 4-t-octylphenyl group, a 4-octyloxyphenyl group, a 4-dodecylphenyl group, and a 1-naphthyl group; an alkenyl group selected from the group consisting of a vinyl group and a 2-allyl group; t-butyl group; a secondary alkyl group selected from the group consisting of an isopropyl group and a 1-ethylpentyl group.

16. The benzoxazole compound as in claim 10, wherein the nucleophilic group is selected from the group consisting of fluorine, a hydroxyl group, an iminoxy group, an amidoxy group, a sulfonamidoxy group, an acyloxy group of carboxylic acid, a carbamoyloxy group, a sulfamoyloxy group, a cyanoxy group, an amino group, a carbonamido group, a sulfonamido group, an ureido group, a sulfamido group, a hydroxylamino group, an imido group, an azido group, an alkylthio group, an arylthio group, a cyanothio group, a sulfo group, a sulfothio group, an alkylsulfonyl group, an arylsulfonyl group, an acylthio group, a thiocarbonylthio group, a cyano group and a substituted or unsubstituted phenoxy group, said substituents being selected from the group consisting of a halogen atom, an alkyl group having 1 to 18 carbon atoms and an alkoxy group having 1 to 6 carbon atoms.

17. A benzoxazole compound of the following formula:

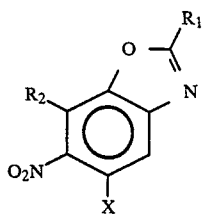

wherein X represents a chlorine atom or a bromine atom, R₁ represents a group selected from the group consisting of a tertiary alkyl group having 4-10 carbon atoms, a 1-methylcyclohexyl group, an adamanthyl group, a heptafluoropropyl group, a secondary alkyl group having 3-7 carbon atoms, a carbamoyl group a ketimine group, a styryl group, a 2-furylvinyl group, an alkenyl group selected from the group consisting of a vinyl group and a 2-allyl group, a heterocyclic residue selected from the group consisting of a 2-furyl group, a 2-pyridyl group, a 3-pyridyl group, a 4-pyridyl group, and a 2-quinolyl group, an unsubstituted phenyl group, a phenyl group substituted with a tertiary alkyl group having 4-8 carbon atoms, and a phenyl group directly substituted by one or more groups selected from the group consisting of halogen atoms, an alkyl group having 1-12 carbon atoms, an alkoxyl group having 1-18 carbon atoms, a secondary alkyl group having 3-8 carbon atoms, a N(CH₃)₂ group and a ketimine group, wherein the number of hydrogen atoms bonded to a carbon atom through which R₁ bonds is either one or zero and R₂ represents a substituent selected from the group consisting of a hydrogen atom, a halogen atom, a lower alkyl group, an alkenyl group selected from the group consisting of a vinyl group and a 2-allyl group, an alkoxyl group having 1-18 carbon atoms, a 2-methoxyethoxy group, an ethylsulfamoyl group, a 2-methoxyethylsulfamoyl group, an acyloxy group of a carboxylic acid, an amido group, a sulfonamido group, an ureido group, an alkyloxycarbonyl group, a carbamoyl group, a sulfamoyl group, a sulfonyl group, a sulfo group, a cyano group, an aryloxy group with the proviso that said aryloxy group is not heteroaromatic.

18. A benzoxazole compound of the following formula:

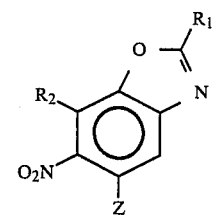

wherein Z represents a nucleophilic group, R₁ represents a group selected from the group consisting of a tertiary alkyl group having 4-10 carbon atoms, a 1-methylcyclohexyl group, an adamanthyl group, a heptafluoropropyl group, a secondary alkyl group having 3-7 carbon atoms, a carbamoyl group, a ketimine group, a styryl group, a 2-furylvinyl group, an alkenyl group selected from the group consisting of a vinyl group and a 2-allyl group, a heterocyclic residue selected from the group consisting of a 2-furyl group, a 3-pyridyl group and a 2-quinolyl group, an unsubstituted phenyl group, a phenyl group substituted with a tertiary alkyl group having 4-8 carbon atoms, and a phenyl group directly substituted by one or more groups selected from the group consisting of halogen atoms, an alkyl group having 1-12 carbon atoms, an alkoxyl group having 1-18 carbon atoms, a secondary alkyl group having 3-8 carbon atoms, a N(CH₃)₂ group and a ketimine group, wherein the number of hydrogen atoms bonded to a carbon atom through which R₁ bonds is either one or zero and R₂ represents a substituent selected from the group consisting of a hydrogen atom, a halogen atom, a lower alkyl group, an alkenyl group selected from the group consisting of a vinyl group and a 2-allyl group, an alkoxy group having 1-18 carbon atoms, a 2-methoxyethoxy group, an ethylsulfamoyl group, a 2-methoxyethylsulfamoyl group, an acyloxy group of a carboxylic acid, an amido group, a sulfonamido group, an ureido group, an alkyloxycarbonyl group, a carbamoyl group, a sulfamoyl group, a sulfonyl group, a sulfo group, a cyano group, an aryloxy group with the proviso that said aryloxy group is not heteroaromatic.

* * * * *